United States Patent [19]
Endo et al.

[11] Patent Number: 4,957,607
[45] Date of Patent: * Sep. 18, 1990

[54] METHOD FOR THE PREPARATION OF A CYCLOALKYL SILANE COMPOUND

[75] Inventors: Mikio Endo, Niigata; Minoru Takamizawa, Moogata; Toshinobu Ishihara; Tohru Kubota, both of Niigata; Toshio Shinohara, Gumma, all of Japan

[73] Assignee: Shin Etsu Chemical Co., Ltd., Tokyo, Japan

[*] Notice: The portion of the term of this patent subsequent to Nov. 28, 2006 has been disclaimed.

[21] Appl. No.: 380,350

[22] Filed: Jul. 17, 1989

Related U.S. Application Data

[63] Continuation-in-part of Ser. No. 154,691, Feb. 11, 1988, Pat. No. 4,883,569.

[30] Foreign Application Priority Data

Feb. 13, 1987 [JP] Japan .................................. 62-30994

[51] Int. Cl.$^5$ .............................................. B01J 19/08
[52] U.S. Cl. ................................ 204/157.74; 556/449
[58] Field of Search ................... 556/479; 204/157.74, 204/157.61, 157.6

[56] References Cited

U.S. PATENT DOCUMENTS

| | | | |
|---|---|---|---|
| 4,038,302 | 7/1977 | Reichel | 556/479 |
| 4,398,010 | 8/1983 | Adkins | 556/10 |
| 4,450,283 | 5/1984 | McAfee | 556/479 |
| 4,530,879 | 7/1985 | Drahnak | 204/157.74 |
| 4,600,484 | 7/1986 | Drahnak | 204/157.74 |

FOREIGN PATENT DOCUMENTS 49-28189  7/1974  Japan .............................. 204/157.74

Primary Examiner—John F. Niebling
Assistant Examiner—Ben C. Hsing
Attorney, Agent, or Firm—Millen, White & Zelano

[57] ABSTRACT

Cycloalkyl silane compounds such as cyclohexyl methyl dichlorosilane can be efficiently prepared by the photochemically induced hydrosilylation reaction. For example, an equimolar mixture of cyclohexene and methyl dichlorosilane with admixture of a catalytic amount of a platinum catalyst, which is an alcohol complex of chloroplatinic acid, is irradiated at a temperature of 70° C. with ultraviolet light so that the hydrosilylation reaction takes place and proceeds almost to completeness without deactivation of the platinum catalyst to give the desired product in a yield of 90% or even higher. Unexpectedly, the efficiency of the reaction can be greatly increased when the platinum catalyst is prepared by heating a solution of chloroplatinic acid in 2-ethylhexyl alcohol at 50° to 80° C. for at least 4 hours.

9 Claims, No Drawings

METHOD FOR THE PREPARATION OF A CYCLOALKYL SILANE COMPOUND

BACKGROUND OF THE INVENTION

This is a continuation-in-part application from a copending U.S. patent application Ser. No. 07/154,691 filed Feb. 11, 1988, now U.S. Pat. No. 4,883,569.

The present invention relates to a method for the preparation of a cycloalkyl silane compound, more particularly, to a method for the preparation of a cycloalkyl silane compound having a saturated cyclic group, which is useful as an intermediate for the synthesis of various kinds of organopolysilanes and organopolysiloxanes and as a silylating agent having stereospecificity, by the hydrosilylation reaction between an unsaturated cyclic hydrocarbon compound such as cyclohexene and a hydrogen silane compound in the presence of a platinum catalyst.

It is well known that cycloalkyl silane compounds having a saturated cyclic hydrocarbon group, such as a cyclohexyl silane compound, can be obtained by the hydrosilylation reaction between an unsaturated cyclic hydrocarbon compound such as cyclohexene and a hydrogen silane compound such as methyl dichlorosilane in the presence of a platinum catalyst. The yield of the desired product is usually low in the above mentioned prior art method and it is generally understood that the yield can be noticeably increased only with extreme difficulties.

To describe a particular prior art method for the preparation of a cycloalkyl silane compound, it has been reported in Journal of the American Chemical Society, volume 79, page 947 (1975) that methyl cyclohexyl dichlorosilane can be obtained almost quantitatively by the reaction of cyclohexene and methyl dichlorosilane in the presence of chloroplatinic acid $H_2PtCl_6.6H_2O$ when the mixture is sealed in a glass ampule and heated in boiling water for 20 hours. This result is, however, not reproducible and the result of subsequently repeated experiments was that the highest yield of the desired reaction product was only about 15% in the reaction mixture and the reaction could proceed no longer even by further continued heating of the mixture. It is also reported in U.S. Pat. No. 3,220,972 that the same cycloalkyl silane compound can be obtained in a yield of 50% by the hydrosilylation reaction of cyclohexene and methyl dichlorosilane in a glass ampule at 100° C. for 6 hours when the reaction is carried out in the presence of an activated platinum catalyst prepared by a heat treatment of a mixture of chloroplatinic acid and n-octyl alcohol. This method is also not totally satisfactory because a yield higher than 50% of the desired product can hardly be obtained due to the deactivation of the platinum catalyst in the course of the reaction.

An attempt has been made and reported in Journal of Organometallic Chemistry, volume 50, page 297 (1973) to perform the above mentioned hydrosilylation reaction in the presence of a nickel complex as the catalyst. This method is industrially not practical because byproducts are necessarily produced in large quantities.

U.S. Pat. Nos. 4,530,879 and 4,600,484 disclose a method in which an SiH-containing organopolysiloxane and an organopolysiloxane having silicon-bonded olefinic groups are reacted at room temperature under irradiation with ultraviolet light in the presence of a platinum complex having an ultraviolet-displaceable group such as cyclooctadienyl, norboradienyl and cyclopentadienyl groups. This method, of course, relates to a reaction between organopolysiloxanes and it is quite unclear in what yield the desired product of the hydrosilylation reaction can be obtained. Chloroplatinic acid or a complex thereof is quite ineffective in such a polymer reaction. Applicability of this particular catalyst to the synthesis of a cycloalkyl silane compound is questionable as to the yield in the reaction between, for example, cyclohexene and methyl dichlorosilane, because the optimum conditions of the hydrosilylation reaction largely depend on the types of the reactant compounds employed, not to mention the extreme expensiveness of such a special platinum catalyst which practically prohibits the application of the method to the industrial production of cycloalkyl silane compounds.

Thus, the only method for the industrial production of a cycloalkyl silane compound having a saturated cyclic hydrocarbon group is the Grignard reaction between a halogen-containing saturated hydrocarbon compound such as chlorocyclohexane and an alkyl halogenosilane such as methyl trichlorosilane. This method by the Grignard reaction is industrially not totally satisfactory with respect to productivity because the reaction must be performed by diluting the reaction mixture with a large volume of a solvent. Also is a magnesium salt is always produced as a by-product and precipitated in the reaction mixture. Therefore, expensive facilities must be provided for the recovery of the solvent and separation of the precipitated magnesium salt, which contributes to an increase in the production cost of the product not to mention the yield of the desired product inherently not being high enough.

SUMMARY OF THE INVENTION

The present invention accordingly has an object to provide an efficient method for the preparation of a cycloalkyl silane compound having a saturated cyclic hydrocarbon group free from the above described problems and disadvantages in the prior art hydrosilylation and Grignard methods.

The method of the present invention for the preparation of a cycloalkyl silane compound comprises:

(A) admixing an unsaturated cyclic hydrocarbon compound represented the general formula $$C_m R^1{}_n A_p, \qquad (I)$$

in which $R^1$ is a hydrogen atom, a fluorine atom or a fluorine-substituted or unsubstituted monovalent hydrocarbon group having 1 to 8 carbon atoms, A is a divalent intramolecular bridging group selected from methylene group $>CH_2$ and dimethylmethylene group $>C(CH_3)_2$, m is an integer of 4 to 8, p is zero or 1 and n is an integer given by $n=2m-2p-2$, with a hydrogen silane compound represented by the general formula $$HR^2{}_q SiX_{3-q}, \qquad (II)$$

in which $R^2$ is an unsubstituted or substituted monovalent hydrocarbon group, X is a halogen atom or an alkoxy group and q is zero, 1 or 2, and an alcoholic complex of chloroplatinic acid prepared by heating chloroplatinic acid in an alcohol at a temperature in the range from 50° to 80° C. for at least 4 hours to form an alcohol complex thereof; and (B) irradiating the reaction mixture with light or, preferably, ultraviolet light to effect the hydrosilylation reaction between the unsaturated cyclic hydrocarbon compound and the hydrogen silane compound.

DETAILED DESCRIPTION OF THE PREFERRED EMBODIMENTS

The above described method of the present invention is characterized by the photochemically induced hydrosilylation reaction taking place in a reaction mixture composed of the above defined unsaturated cyclic hydrocarbon compound and hydrogen silane compound with admixture of a catalytic amount of a platinum catalyst. Advantageously and quite unexpectedly, the platinum catalyst under irradiation with light is not deactivated during the reaction so that the reaction can proceed almost to completion to give the desired cycloalkyl silane compound in a yield of 90% or even higher. For example, the reaction is complete within 10 hours at 70° C. under normal pressure so that the method is industrially advantageous for the preparation of a cycloalkyl silane compound.

One of the reactants in the inventive method is an unsaturated cyclic hydrocarbon compound represented by the above given general formula $C_mR^1{}_nA_p$. In the formula, $R^1$ is a hydrogen atom, a fluorine atom or a monovalent hydrocarbon group having 1 to 8 carbon atoms such as alkyl groups, e.g., methyl, ethyl, propyl, butyl and octyl groups, and aryl groups, e.g., phenyl and tolyl groups, optionally, substituted by a fluorine atom or atoms for a part or all of the hydrogen atoms in the above named hydrocarbon groups. The symbol A in the formula denotes a divalent intramolecular bridging group selected from methylene group $>CH_2$ and dimethylmethylene group $>C(CH_3)_2$. The subscript m is an integer of 4 to 8, p is zero or 1 and n is an integer given by $n=2m-2p-2$.

The unsaturated hydrocarbon compounds in conformity with the general formula (I) and definitions of the symbols therein include cyclohexene $C_6H_{10}$, cycloheptene $C_7H_{12}$, 1-methyl-1-cyclohexene $C_6H_9CH_3$, 4-methyl-1-cyclohexene $C_6H_9CH_3$, norbornylene, 5-perfluorohexyl norbornylene, bornylene and the like. The unsaturated cyclic hydrocarbon compound as the reactant in the inventive method should of course be selected from the above named compounds and the like corresponding to the desired product.

The other reactant to be reacted with the above described unsaturated cyclic hydrocarbon compound is a hydrogen silane compound represented by the general formula $HR^2{}_qSiX_{3-q}$ wherein $R^2$ is a monovalent hydrocarbon group such as alkyl groups, e.g., methyl, ethyl, propyl and butyl groups, and aryl groups, e.g., phenyl and tolyl group, as well as those substituted groups obtained by replacing a part or all of the hydrogen atoms in the above named hydrocarbon groups with substituents such as halogen atoms, cyano groups and the like, e.g., chloromethyl, 3,3,3-trifluoropropyl and 2-cyanoethyl groups. The symbol X in the formula denotes an atom of halogen, e.g., chlorine, bromine and iodine, or an alkoxy group, e.g., methoxy, ethoxy, propoxy and butoxy groups. The subscript q is zero, 1 or 2. Suitable hydrogen silane compounds include trichlorosilane, methyl dichlorosilane, dimethyl chlorosilane, trimethoxy silane, methyl diethoxy silane and the like.

The platinum compound used as the catalyst for the hydrosilylation reaction may be any of the known platinum compounds used conventionally in the hydrosilylation reaction but it is preferably chloroplatinic acid which is used either as such or in the form of a solution in an alcoholic solvent or a complex compound with an olefin or vinyl siloxane. Most preferably, the platinum catalyst is prepared by dissolving chloroplatinic acid $H_2PtCl_6.6H_2O$ in an alcohol, such as isopropyl alcohol, n-butyl alcohol, n-octyl alcohol and 2-ethylhexyl alcohol, in an amount of, for example, 10 to 30 g per gram of chloroplatinic acid $H_2PtCl_6.6H_2O$ and heating the solution at a temperature in the range from 50° to 80° C. for a length of time of at least 4 hours or, preferably, from 5 to 6 hours followed by stripping of the volatiles such as hydrogen chloride, water and unreacted alcohol, under a reduced pressure of, for example, 20 to 50 mmHg at the same temperature as above. The amount of the platinum catalyst added to the reaction mixture is not particularly limitative provided that a substantial promoting effect can be obtained on the velocity of the hydrosilylation. The amount should usually be at least 20 ppm or, preferably, at least 40 ppm by weight calculated as platinum based on the amount of the hydrogen silane compound.

The method of the invention is performed by irradiating the reaction mixture prepared by mixing the above described unsaturated cyclic hydrocarbon compound, hydrogen silane compound and platinum catalyst with light to effect the hydrosilylation reaction. The nature of the light is not particularly limitative and the reaction can proceed, for example, by exposing the reaction mixture to sunlight. It is industrially preferable, however, that the light is ultraviolet light emitted from a suitable ultraviolet lamp such as low-pressure and high-pressure mercury lamps.

The hydrosilylation reaction of the invention method is performed by introducing the unsaturated cyclic hydrocarbon compound and the hydrogen silane compound together with a platinum compound into a reaction vessel having a window for ultraviolet irradiation and equipped with a reflux condenser and stirrer equipment and irradiating the reaction mixture in the vessel with ultraviolet light through the window. The amounts of the unsaturated cyclic hydrocarbon compound and the hydrogen silane compound should usually be equimolar but it is optional to increase the amount of either one of the reactants over equimolar according to need. It is advantageous from the standpoint of safety that the unsaturated cyclic hydrocarbon compound and the platinum compound are first introduced into the reaction vessel and the hydrogen silane compound is added dropwise into the mixture in the vessel under agitation because the hydrogen silane compound itself is subject to a disproportionation reaction under the reaction conditions.

Although the hydrosilylation reaction of the inventive method can proceed at room temperature, the reaction mixture may be heated at 50° to 80° C. or, preferably, 60° to 70° C. when acceleration of the reaction is desired. An excessively high temperature of, for example, 80° C. or higher is undersirable because the reaction velocity is decreased at such a high temperature. The reaction mixture to be irradiated with ultraviolet light is prepared usually without using any solvent but it is optional to dilute the reaction mixture with a suitable inert organic solvent such as octane, toluene, xylene and the like according to need.

In the following, the method of the invention is described in more detail by way of examples and comparative examples.

Preparation of a platinum catalyst.

Into a glass-made flask of 200 ml capacity equipped with a stirrer, reflux condenser, thermometer and dropping funnel were added 5 g of chloroplatinic acid $H_2PtCl_6.6H_2O$ followed by 95 g of 2-ethylhexyl alcohol were added thereto dropwise through the dropping funnel under agitation at room temperature. The chloroplatinic acid was dissolved in the alcohol to give a clear solution.

Thereafter, the mixture in the flask was heated at 70° to 80° C. under reflux for 5 to 6 hours under continued agitation and then the mixture was stripped of volatile matters under a reduced pressure of 15 mmHg at the same temperature as above with continued agitation. In this manner, 95 g of a liquid were obtained which contained 2% by weight of platinum.

EXAMPLE 1 AND COMPARATIVE EXAMPLE 1

Cyclohexene and methyl dichlorosilane each in an amount of 1.0 mole were introduced into a glass-made reaction vessel of 250 ml capacity equipped with a reflux condenser and stirrer equipment and having a window for irradiation with light together with 0.43 g of the platinum catalyst solution prepared above to form a reaction mixture. The amount of the platinum catalyst corresponded to 200 ppm by weight calculated as $H_2PtCl_6.6H_2O$ based on the amount of methyl dichlorosilane.

The thus prepared reaction mixture was irradiated at 20° C. with ultraviolet light emitted from a high-pressure mercury lamp (Model UN-102, manufactured by Ushio Electric Co.) so that the hydrosilylation reaction between the reactants proceeded exothermically to increase the temperature of the reaction mixture by 5° to 6° C. above the starting temperature until the reaction neared completion after 40 hours of the ultraviolet irradiation. Thereafter, the reaction mixture was subjected to distillation to give the desired cylohexyl methyl dichlorosilane in a yield of about 90%.

For comparison, an attempt was made to perform the hydrosilylation reaction in the same reaction mixture as above by heating the reaction mixture under reflux without irradiation with ultraviolet light. The temperature of the reaction mixture was 55° C. at the start of the reaction and gradually increased up to 71° C. after 20 hours to level off. Analysis of the thus obtained reaction mixture indicated that the yield of the desired cyclohexyl methyl dichlorosilane was only 9%. No improvement could be obtained in the yield of the product by further continued heating of the reaction mixture.

For further comparison, a hydrosilylation reaction of the same reaction mixture otherwise corresponding to the above except for an increase of the amount of the platinum catalyst to 1.08 g corresponding to 500 ppm as $H_2PtCl_6.6H_2O$ based on the amount of methyl dichlorosilane was performed in a stainless steel-made autoclave equipped with a stirrer by heating the reaction mixture at 100° C. The yield of cyclohexyl methyl dichlorosilane was 32% after 7 hours of reaction, increased to 34% and then essentially leveled off according to the results of the gas chromatographic analysis. Distillation of the reaction mixture gave the desired product in a yield of only 30% based on the theoretical value.

EXAMPLE 2

Into the same reaction vessel as used in Example 1 was introduced 1.0 mole of cyclohexene admixed with 0.21 g of the same platinum catalyst as used in Example 1 and the mixture in the vessel was heated at 70° C. Thereafter, 0.5 mole of methyl dichlorosilane was added dropwise to the mixture in the reaction vessel. There was almost no indication of the reaction proceeding as long as the reaction vessel was kept in dark.

The reaction mixture in the vessel was then irradiated with ultraviolet light emitted from a high-pressure mercury lamp, which caused the reaction to take place. Methyl dichlorosilane was further added to the reaction mixture dropwise in an additional amount of 0.7 mole and the reaction was continued under irradiation with ultraviolet light until the reaction was nearly completed after 8 hours. Distillation of the thus obtained reaction mixture after completion of the reaction gave the desired cyclohexyl methyl dichlorosilane in a yield of 95%.

EXAMPLE 3

Into the same reaction vessel as used in Example 1 was introduced 1.0 mole of cyclohexene with admixture of 0.18 g of the same platinum catalyst as used in Example 1 and the mixture in the vessel was heated at 70° C. Thereafter, 1.0 mole of methyl dichlorosilane was added dropwise into the reaction mixture in the vessel under irradiation with ultraviolet light emitted from a high-pressure mercury lamp. The reaction, which started immediately was completed after 10 hours. Distillation of the reaction mixture thus obtained gave the desired cyclohexyl methyl dichlorosilane in a yield 85%.

EXAMPLE 4

Into the same reaction vessel as used in Example 1 was introduced 1.0 mole of cyclopentene admixed with 0.50 g of the same platinum catalyst as used in Example 1 and the mixture in the vessel was heated at 40° C. Thereafter, 10 moles of trichlorosilane were added dropwise to the mixture in the reaction vessel under irradiation with ultraviolet light emitted from a high-pressure mercury lamp. The reaction was completed after 6 hours. Distillation of the thus obtained reaction mixture gave the desired cyclopentyl trichlorosilane in a yield of 93%.

EXAMPLE 5

Into the same reaction vessel as used in Example 1 was introduced 1.0 mole of cyclooctene admixed with 0.22 g of the same platinum catalyst as used in Example 1 and the mixture was heated at 70° C. Thereafter, 1.0 mole of methyl dichlorosilane was added dropwise to the mixture in the reaction vessel under irradiation with ultraviolet light emitted from a high-pressure mercury lamp. The reaction was completed within 10 hours. Distillation of the thus obtained reaction mixture gave the desired cyclooctyl methyl dichlorosilane in a yield of 90%.

EXAMPLE 6

Into the same reaction vessel as used in Example 1 was introduced 1.0 mole of norbornylene with admixture of 0.22 g of the same platinum catalyst as used in Example 1 and the mixture in the vessel was heated at 70° C. Thereafter, 1.0 mole of methyl dichlorosilane was added dropwise into the mixture in the reaction vessel under irradiation with ultraviolet light emitted from a low-pressure mercury lamp (model LP-11B, manufactured by Toshiba Corp.). The reaction was completed within 6 hours. Distillation of the thus obtained reaction mixture gave the desired norbornyl methyl dichlorosilane in a yield of 91%.

EXAMPLE 7

Into the same reaction vessel as used in Example 1 was introduced 1.0 mole of 5-perfluorohexyl norbornylene admixed with 0.06 g of the same solution of platinum catalyst as used in Example 1 and the mixture was heated at 70° C. Thereafter, 1.0 mole of methyl dichlorosilane was added dropwise to the mixture in the reaction vessel under irradiation with ultraviolet light emitted from a high-pressure mercury lamp. The reaction was completed within 6 hours. Distillation of the thus obtained reaction mixture gave the desired 5-perfluorohexylnorbornyl methyl dichlorosilane in a yield of 90%.

EXAMPLE 8

Into the same reaction vessel as used in Example 1 was introduced 1.0 mole of cyclohexene admixed with 0.23 g of the same platinum catalyst as used in Example 1 and the mixture was heated at 70° C. Thereafter, 1.0 mole of trimethoxy silane was added dropwise into the mixture in the reaction vessel under irradiation with ultraviolet light emitted from a high-pressure mercury lamp. The reaction was completed within 7 hours. Distillation of the thus obtained reaction mixture gave the desired cyclohexyl trimethoxy silane in a yield of 91%.

EXAMPLE 9

Into a glass-made flask of 100 ml capacity equipped with a reflux condenser and stirrer were introduced 0.25 mole of cyclohexene, 0.25 mole of methyl dichlorosilane and 0.11 g of the same platinum catalyst as used in Example 1 and the flask containing the mixture was put under direct sun light at room temperature. A reaction took place in the mixture and continued without loss of the catalyst activity. The reaction was almost complete after 70 hours of exposure to sun light. Distillation of the thus obtained reaction mixture gave cyclohexyl methyl dichlorosilane in a yield of 91%.

What is claimed is:

1. A method for the preparation of a cycloalkyl silane compound which comprises the steps of:
   (A) admixing an unsaturated cyclic hydrocarbon compound represented by the general formula $C_m R^1_n A_p$, in which $R^1$ is a hydrogen atom, a fluorine atom or a flourine-substituted or unsubstituted monovalent hydrocarbon group having 1 to 8 carbon atoms, A is a divalent intramolecular bridging group selected from methylene group $>CH_2$ and dimethylmethylene group $>C(CH_3)_2$, m is an integer of 4 to 8, p is zero or 1 and n is an integer given by the equation $n = 2m - 2p - 2$, with a hydrogen silane compound represented by the general formula $HR^2_q SiX_{3-q}$, in which $R^2$ is an unsubstituted or substituted monovalent hydrocarbon group, X is a halogen atom or an alkoxy group and q is zero, 1 or 2, and an alcoholic complex of chloroplatinic acid prepared by heating chloroplatinic acid in an alcohol at a temperature in the range from 50° to 80° C. for at least 4 hours to form an alcohol complex thereof; and
   (B) irradiating the reaction mixture with ultraviolet light to effect the hydrosilylation reaction between the unsaturated cyclic hydrocarbon compound and the hydrogen silane compound.

2. The method for the preparation of a cycloalkyl silane compound as claimed in claim 1 wherein the alcohol is 2-ethylhexyl alcohol.

3. The method as claimed in claim 1, wherein the cyclic hydrocarbon is cyclohexane, cycloheptane, 1-methyl-1-cyclohexene, 4-methyl-1-cyclohexene, norbornylene, 5-perfluorohexyl norbornylene or bornylene.

4. The method as claimed in claim 1, wherein X in the formula is chlorine or alkoxy and $R^2$ is methyl, ethyl, propyl, butyl, phenyl, tolyl or a corresponding group substituted with halogen or cyano.

5. The method as claimed in claim 4, wherein the hydrogensilane compound is trichlisosilane, methyldichlorosilane, dimethyl chlorosilane, trimethoxy silane, or methyl diethoxy silane.

6. The method as claimed in claim 1, wherein the amount of the alcoholic complex of chloroplatinic acid employed provides at least 40 ppm, calculated as platinum, based on the hydrogen silane compound.

7. The method as claimed in claim 1, wherein the reaction is conducted at 60° to 70° C.

8. The method as claimed in claim 1, wherein the cyclic hydrocarbon is cyclohexane, cycloheptane, 1-methyl-1-cyclohexene, 4-methyl-1-cyclohexene, norbornylene, 5-per-fluorohexyl norbornylene, or bornylene; wherein the hydrogensilane compound is trichlisosilane, methyldichlorosilane, dimethyl chlorosilane, trimethoxy silane, or methyl diethoxy silane; wherein the amount of the alcoholic complex of chloroplatinic acid employed provides at least 40 ppm, calculated as platinum, based on the hydrogen silane compound; and wherein the reaction is conducted at 60° to 70° C.

9. The method for the preparation of a cycloalkyl silane compound as claimed in claim 8 wherein the alcohol is 2-ethylhexyl alcohol.

* * * * *